US00PP13937P29

(12) United States Plant Patent
Bergman

(10) Patent No.: US PP13,937 P2
(45) Date of Patent: Jul. 8, 2003

(54) CHRYSANTHEMUM PLANT NAMED 'YOOAKLAND'

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/094,326

(22) Filed: Mar. 8, 2002

(51) Int. Cl.[7] ..... A01H 5/00
(52) U.S. Cl. ..... Plt./288

(58) Field of Search ..... Plt./288, 287

*Primary Examiner*—Bruce R. Campell
*Assistant Examiner*—June Hwu
(74) *Attorney, Agent, or Firm*—C. A. Whealy

(57) ABSTRACT

A distinct cultivar of Chrysanthemum plant named 'Yooakland', characterized by its uniform, upright and compact plant habit; strong and freely branching growth habit; dense dark green foliage; uniform and early flowering habit; decorative-type inflorescences with white-colored ray florets; excellent postproduction longevity with plants maintaining good substance and color for about four weeks in an interior environment; and tolerance to high production temperatures.

1 Drawing Sheet

BOTANICAL CLASSIFICATION/CULTIVAR DESIGNATION

*Chrysanthemum×morifolium* cultivar Yooakland.

BACKGROUND OF THE INVENTION

The present Invention relates to a new and distinct cultivar of Chrysanthemum plant, botanically known as *Chrysanthemum×morifolium* and hereinafter referred to by the name 'Yooakland'.

The new Chrysanthemum is a product of a planned breeding program conducted by the Inventor in Salinas, Calif. and Fort Myers, Fla. The objective of the breeding program is to create new potted Chrysanthemum cultivars that are suitable for year-round production with uniform plant growth habit, good vigor, desirable inflorescence form and floret colors, fast response time, and good postproduction longevity.

The new Chrysanthemum originated from a cross made by the Inventor in February, 1997, in Salinas, Calif., of a proprietary Chrysanthemum seedling selection identified as code number YB-4496, not patented, as the female, or seed, parent with a proprietary Chrysanthemum seedling selection identified as code number YB-1521, not patented, as the male, or pollen, parent. The new Chrysanthemum was discovered and selected by the Inventor as a single flowering plant within the progeny of the stated cross grown in a controlled environment in Salinas, Calif. The selection of this plant was based on its uniform plant growth habit, desirable inflorescence form and ray floret color, fast response time, and excellent postproduction longevity.

Asexual reproduction of the new Chrysanthemum by vegetative tip cuttings was first conducted in Fort Myers, Fla. in February, 1998. Asexual reproduction by cuttings has shown that the unique features of this new Chrysanthemum are stable and reproduced true to type in successive generations.

SUMMARY OF THE INVENTION

The cultivar Yooakland has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yooakland'. These characteristics in combination distinguish 'Yooakland' as a new and distinct Chrysanthemum:

1. Uniform, upright and compact plant habit.
2. Strong and freely branching growth habit.
3. Dense dark green foliage.
4. Uniform flowering habit.
5. Early flowering, eight-week response time.
6. Decorative-type inflorescences.
7. White-colored ray florets.
8. Excellent postproduction longevity with plants maintaining good substance and color for about four weeks in an interior environment.
9. Tolerance to high production temperatures.

Compared to plants of the female parent selection, plants of the new Chrysanthemum have a fewer disc florets and are more tolerant to high production temperatures.

Compared to plants of the male parent selection, plants of the new Chrysanthemum are more compact, flower more uniformly and have fewer disc florets.

Plants of the new Chrysanthemum can be compared to plants of the cultivar Surf, disclosed in U.S. Plant Pat. No. 4,585. In side-by-side comparisons conducted by the Inventor in Salinas, Calif., plants of the new Chrysanthemum differed from plants of the cultivar Surf in the following characteristics:

1. Plants of the new Chrysanthemum flowered one to two days earlier than plants of the cultivar Surf.
2. Plants of the new maintained inflorescence form better over time than plants of the cultivar Surf.

3. Under low production temperatures, ray florets of plants of the new Chrysanthemum did not develop a pink cast whereas ray florets of plants of the cultivar Surf did develop a pink cast.

4. Plants of the new Chrysanthemum were more tolerant to high production temperatures than plants of the cultivar Surf.

Plants of the new Chrysanthemum can also be compared to plants of the cultivar Yotrenton, disclosed in U.S. Plant Pat. No. 12,789. In side-by-side comparisons conducted by the Inventor in Salinas, Calif., plants of the new Chrysanthemum differed from plants of the cultivar Yotrenton in the following characteristics:

1. Plants of the new Chrysanthemum were more upright and stronger than plants of the cultivar Yotrenton.

2. Plants of the new Chrysanthemum were more tolerant to high production temperatures than plants of the cultivar Yotrenton.

Plants of the new Chrysanthemum can also be compared to plants of the cultivar Yohomestead, disclosed in a U.S. Plant patent application Ser. No. 10/094,271 filed concurrently. In side-by-side comparisons conducted by the Inventor in Salinas, Calif., plants of the new Chrysanthemum differed from plants of the cultivar Yohomedstead in the following characteristics:

1. Plants of the new Chrysanthemum were shorter and more outwardly spreading than plants of the cultivar Yooakland.

2. Leaves of plants of the new Chrysanthemum were longer, narrower and had longer petioles than plants of the cultivar Yooakland.

3. Ray florets of plants of the new Chrysanthemum were more incurved than ray florets of plants of the cultivar Yooakland.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph at the top of the sheet comprises a side perspective view of a typical flowering plant of 'Yooakland' grown as a disbud-type.

The photograph at the bottom of the sheet comprises a close-up view of typical inflorescences of 'Yooakland' grown as a disbud-type.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered during the winter in Salinas, Calif., in a fiberglass-covered greenhouse and under conditions which approximate those generally used in commercial potted Chrysanthemum production. During the production of these plants, the following conditions were measured: day temperatures, 21 to 27° C.; night temperatures, 17 to 19° C.; and light levels, 5,000 to 6,000 foot-candles. Four unrooted cuttings were directly stuck in 15-cm containers, exposed to long day/short night conditions, and pinched once about 14 days later. One week after the pinch, the photoinductive short day/long night treatments were initiated. Plants used for the photographs and description were grown as disbud-types. Measurements and numerical values represent averages of typical flowering plants.

Botanical classification: *Chrysanthemum×morifolium* cultivar Yooakland.

Commercial classification: Decorative-type potted Chrysanthemum.

Parentage:

*Female, or seed, parent.*—Proprietary *Chrysanthemum×morifolium* seedling selection identified as code number YB-4496, not patented.

*Male, or pollen, parent.*—Proprietary *Chrysanthemum×morifolium* seedling selection identified as code number YB-1521, not patented.

Propagation:

*Type.*—Terminal tip cuttings.

*Time to initiate roots.*—About four days at 21° C.

*Time to produce a rooted cutting.*—About ten days at 21° C.

*Root description.*—White, close to 155D; fibrous.

*Rooting habit.*—Freely branching.

Plant description:

*Appearance.*—Herbaceous decorative-type potted Chrysanthemum that can be grown as a disbud or as a spray-type. Stems mostly upright and somewhat outwardly spreading; uniform crown. Freely branching, about three to four lateral branches develop after removal of terminal apex (pinching); dense and full plants.

*Plant height.*—About 22 cm.

*Plant width.*—About 49 cm.

*Lateral branches* (*peduncles*).—Length: About 15 cm. Diameter: About 4 mm. Internode length: About 9 mm. Strength: Strong. Texture: Pubescent. Color: Close to 146A.

*Foliage description.*—Arrangement: Alternate. Length: About 10.4 cm. Width: About 6.5 cm. Apex: Cuspidate to mucronate. Base: Truncate. Margin: Palmately lobed, sinuses between lateral lobes parallel to divergent. Texture: Upper surface: Sparsely pubescent. Lower surface: Pubescent; veins prominent. Color: Young and mature foliage, upper surface: Close to 147A. Young and mature foliage, lower surface: Close to 147B. Venation, upper surface: Close to 147A. Venation, lower surface: Close to 147B. Petiole length: About 3.2 cm. Petiole diameter: About 2 mm. Petiole color, both surfaces: Close to 146A to 146B.

Inflorescence description:

*Appearance.*—Decorative-type inflorescence form with elongated oblong-shaped ray florets. Inflorescences borne on terminals above foliage. Disk and ray florets arranged acropetally on a capitulum. Not fragrant. Can be grown as a disbud or spray-type.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to three weeks of long day/short night conditions followed by photoinductive short day/long night conditions flower about eight weeks later.

*Postproduction longevity.*—Inflorescences maintain good color and substance for at about four weeks in an interior environment.

*Quantity of inflorescences.*—Grown as a disbud-type, only one inflorescence, the terminal inflorescence, develops per lateral branch.

*Inflorescence bud.*—Height: About 8 mm. Diameter: About 9 mm. Shape: Oblate. Color: Close to 147A.

*Inflorescence size.*—Diameter: About 9.8 cm. Depth (height): About 3.9 cm. Diameter of disc: About 3.5 mm, inconspicuous. Receptacle diameter: About 9 mm.

*Ray florets.*—Shape: Elongated-oblong. Orientation: Initially upright, then perpendicular to the peduncle, reflexed with subsequent development. Aspect: Mostly incurved. Length: About 4.8 cm. Width: About 1.3 cm. Apex: Emarginate or rounded. Base: Fused into a corolla tube. Corolla tube length: About 9 mm. Margin: Entire. Texture: Smooth, glabrous, satiny. Number of ray florets per inflorescence: About 268 arranged in numerous rows. Color: When opening, upper and lower surfaces: Closest to 155D. Fully expanded, upper and lower surfaces: Closest to 155D.

*Disc florets.*—Arrangement: Massed at center of receptacle. Shape: Tubular, elongated. Apex: Five-pointed. Length: About 6 mm. Width: Apex: About 2 mm. Base: About 1 mm. Number of disc florets per inflorescence: Less than 50. Color: Immature: 154A. Mature: Apex: Close to 12A. Mid-section and base: Close to 146C.

*Phyllaries.*—Quantity per inflorescence: About 32. Length: About 1 cm. Width: About 3.5 mm. Shape: Ligulate. Apex: Acute. Base: Truncate. Texture: Upper surface: Waxy, smooth. Lower surface: Pubescent. Color: Upper surface: Between 146A and 147A. Lower surface: Close to 147A.

*Reproductive organs.*—Androecium: Present on disc florets only. Anther color: 12A. Pollen amount: Scarce. Pollen color: 15A. Gynoecium: Present on both ray and disc florets. Style color: Close to 146C. Stigma color: Close to 12A.

*Seed.*—Seed production has not been observed.

Disease resistance: Resistance to pathogens common to Chrysanthemums has not been observed on plants grown under commercial greenhouse conditions.

High temperature tolerance: Plants of the new Chrysanthemum have been observed to be tolerant to high temperature conditions when grown during the summer under greenhouse conditions in southwest Florida.

It is claimed:

1. A new and distinct cultivar of Chrysanthemum plant named 'Yooakland', as illustrated and described.

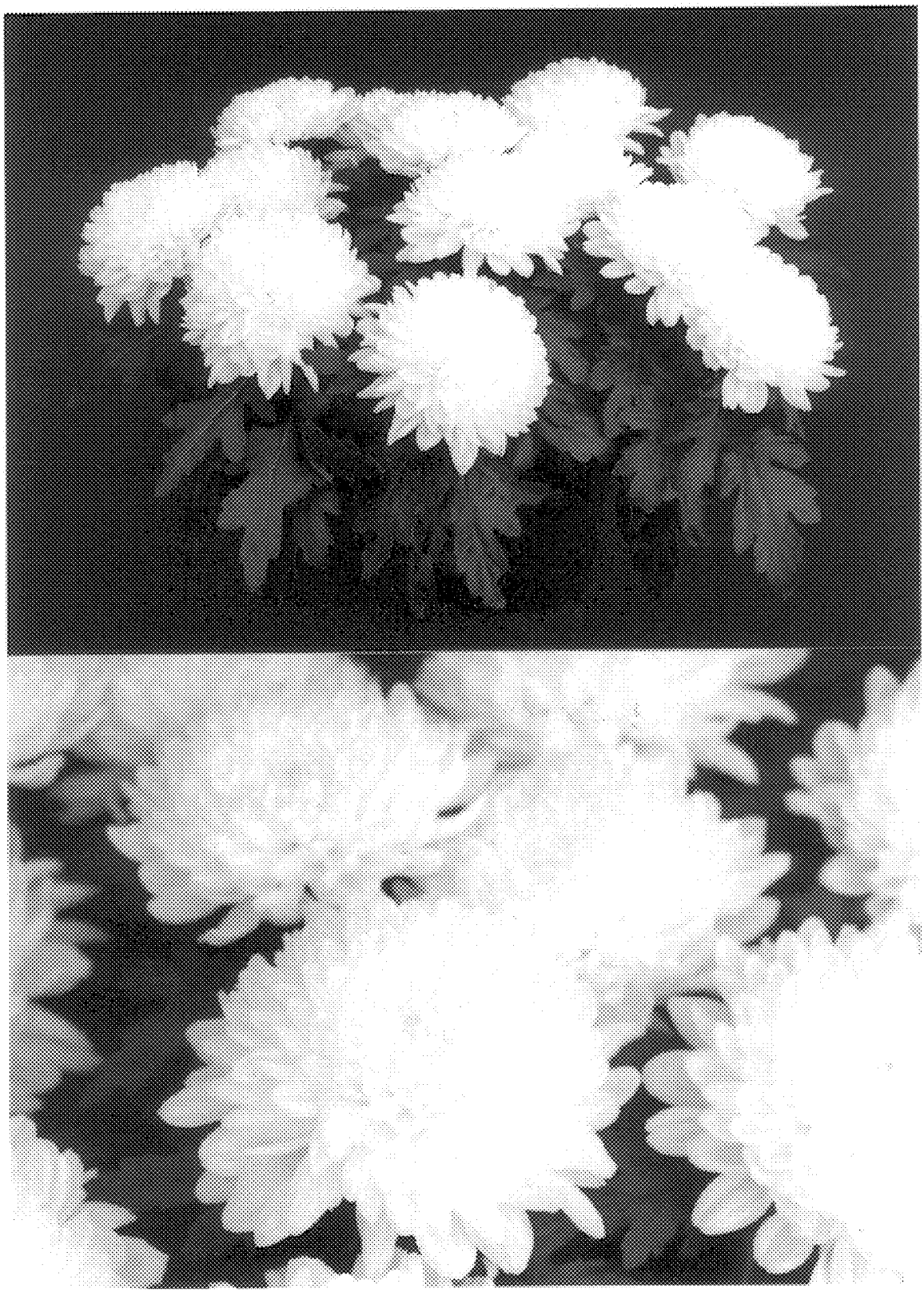

* * * * *